United States Patent
Yla-Herttuala et al.

(10) Patent No.: US 7,208,291 B2
(45) Date of Patent: Apr. 24, 2007

(54) NUCLEIC ACIDS ENCODING BIOTIN-BINDING RECEPTORS

(75) Inventors: Seppo Yla-Herttuala, Kuopio (FI); Markku Kulomaa, Jyvaskyla (FI); Pauliina Lehtolainen, Kuopio (FI); Varpu Marjomaki, Jyvaskyla (FI); Kari Airenne, Jyvaskyla (FI)

(73) Assignee: Ark Therapeutics Limited (GB)

( * ) Notice: Subject to any disclaimer, the term of this patent is extended or adjusted under 35 U.S.C. 154(b) by 475 days.

(21) Appl. No.: 10/618,570

(22) Filed: Jul. 11, 2003

(65) Prior Publication Data

US 2004/0185059 A1 Sep. 23, 2004

Related U.S. Application Data

(63) Continuation of application No. 09/622,804, filed as application No. PCT/GB99/00546 on Feb. 23, 1999, now abandoned.

(30) Foreign Application Priority Data

Feb. 23, 1998 (GB) ................. 9803757.5
Jun. 24, 1998 (GB) ................. 9813653.4

(51) Int. Cl.
  C12N 15/00 (2006.01)
  C12N 15/63 (2006.01)
  C07H 21/04 (2006.01)

(52) U.S. Cl. ................. 435/69.1; 435/320.1; 536/23.4

(58) Field of Classification Search ................. None
See application file for complete search history.

(56) References Cited

U.S. PATENT DOCUMENTS 5,457,035 A  10/1995 Baum et al.
5,510,466 A   4/1996 Krieger et al.

FOREIGN PATENT DOCUMENTS

| EP | 03/59347 | 3/1990 |
|---|---|---|
| WO | WO 87/05026 | 8/1987 |
| WO | WO 96/40761 A1 | 12/1996 |
| WO | WO 97/19957 | 6/1997 |

OTHER PUBLICATIONS

Rihova, B., "Targeting of Drugs to Cell Surface Receptors," *Critical Reviews in Biotechnology* 1997, vol. 17, No. 2, pp. 149-169.
Kulomaa, M. S. et al., "A Production of Recombinant Avidin and Avidin-Fusion Proteins in Bacterial and Insect Cells", *FASEB Journal* 1995, vol. 9, No. 6, p. A1395, XP-002112828, abstract only.
Marjomaki, V. et al., "Efficient Transport of Avidin Fusion Proteins Into Late and Early Endosomes", *Molecular Biology of the Cell* 1996, vol. 7 (Supp. S), p. 2631, XP-002112829, abstract only.

*Primary Examiner*—Ruixiang Li
(74) *Attorney, Agent, or Firm*—Saliwanchik, Lloyd & Saliwanchik

(57) ABSTRACT

The present invention pertains to a novel transmembrane protein capable of binding to biotinylated molecules, the protein comprising a cytoplasmic domain, a membrane-spanning domain and an extracellular domain, wherein the extracellular domain comprises biotin-binding activity.

5 Claims, 3 Drawing Sheets

NUCLEIC ACIDS ENCODING BIOTIN-BINDING RECEPTORS

CROSS-REFERENCE TO RELATED APPLICATION

Figure 1:
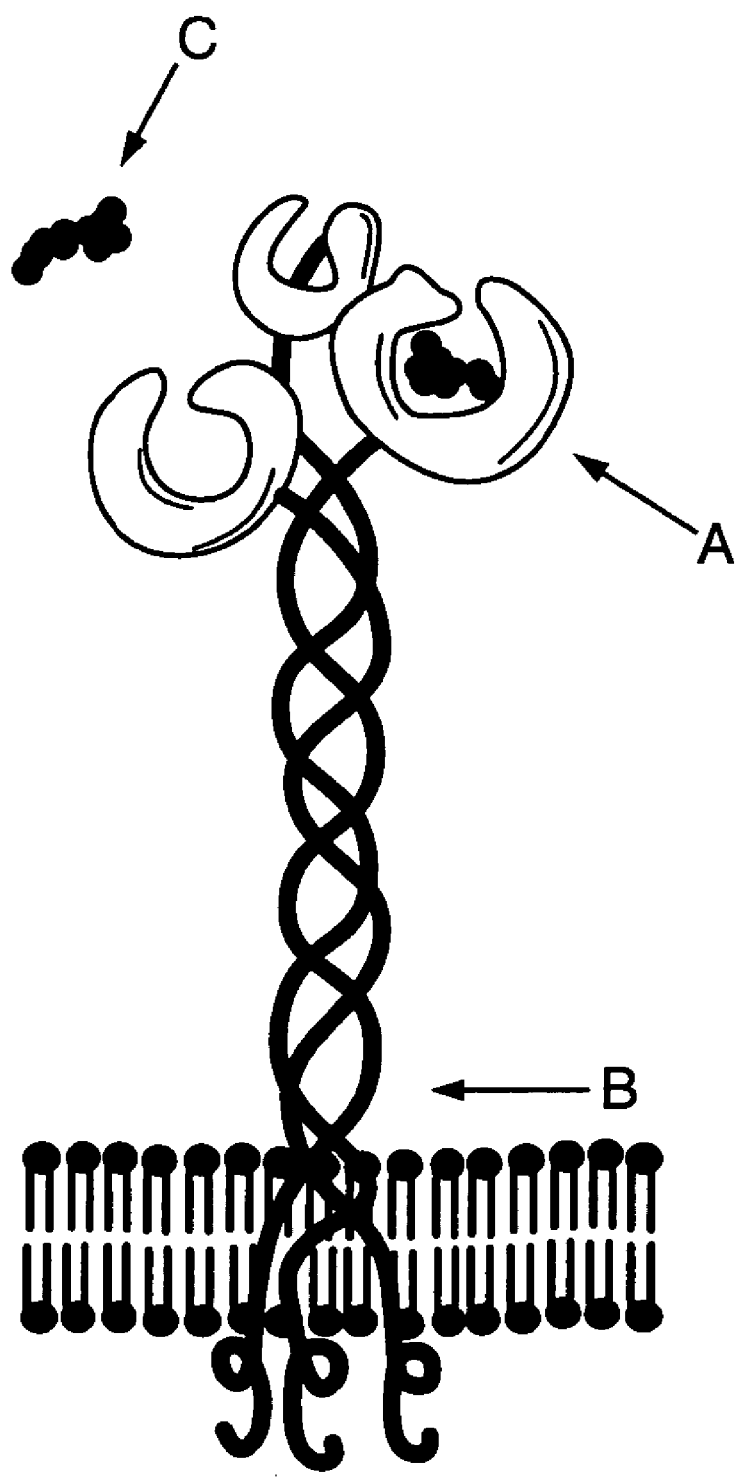

This application is a continuation of U.S. application Ser. No. 09/622,804, filed Aug. 22, 2000, now abandoned which is the U.S. national stage of international application No. PCT/GB99/00546, filed Feb. 23, 1999.

FIELD OF THE INVENTION

This invention relates to membrane-spanning proteins having biotin-binding activity.

BACKGROUND TO THE INVENTION

Biotin (vitamin H) is a readily water-soluble substance found at low concentrations in blood and tissues. The biological role of biotin is as a carrier of activated $CO_2$ and it permits the transfer of $CO_2$ to acceptors without the need for additional free energy. The activated carboxybiotin is usually attached to an enzyme that is required for the formation of carboxybiotin. For example, biotin may be attached to pyruvate carboxylase which, in the presence of acetyl CoA, catalyses the formation of carboxybiotin and the subsequent transfer of the activated carboxyl group to pyruvate, to form oxaloacetate.

Biotin also binds with one of the highest naturally known affinities to avidin, a 63 kDa glycoprotein from chicken egg white, and to streptavidin, a non-glycosylated protein from the bacterium *Streptomyces avidinii*. The binding is almost irreversible in character (Ka $10^{15}$ $mol^{-1}$). The affinity between avidin and biotin has proved very useful in a wide variety of bioanalytical applications. For example, the avidin-biotin complex has been used successfully in a wide variety of detection systems where target molecules are combined with biotin through its carboxy terminus, to form biotinylated molecules which may be easily detected or separated from solution. Biotinylation can occur without changing the biological or physiochemical properties of the various molecules and without affecting the binding capacity of the biotin prosthetic group to avidin.

SUMMARY OF THE INVENTION

It has now been realised that the biotin-binding activity of avidin and streptavidin may be utilised in the production of transmembrane proteins capable of binding biotinylated molecules.

Proteins of the present invention may comprise a cytoplasmic domain, a membrane-spanning domain and an extracellular domain, wherein the extracellular domain comprises biotin-binding activity. The extracellular domain may comprise avidin or streptavidin functional activity.

Using proteins or nucleic acid molecules of this invention, it is possible to target biotinylated molecules to specific sites in tissues. Molecules targeted in this way may be taken up by the tissues or cells by endocytosis, allowing the molecules to exert their effects within or on the cell.

DESCRIPTION OF THE DRAWINGS

FIG. 1 is a schematic illustration of a fusion protein of the present invention, where A represents avidin and B represents the membrane-spanning domain of an endocytotic receptor (and C represents biotin);

FIG. 2 is a schematic illustration of a cloning strategy using a shuttle vector; and FIG. 3 is a schematic illustration of a cloning strategy using a retrovirus vector.

DESCRIPTION OF THE INVENTION

Proteins of the present invention may be produced using conventional recombinant DNA technology. Typically, a DNA sequence coding for the functional domain of a biotin-binding protein such as avidin, streptavidin or a related protein, is engineered into a genetic construct which comprises a DNA sequence coding for a protein having membrane-spanning properties. Examples of avidin and streptavidin-related proteins include AVR-1-AVR-5, AVR-X-AVR-V, Stv1 and Stv2.

The individual domains of the fusion protein may be amplified by polymerase chain reaction or isolated from the parent cDNA using restriction enzyme digestion, isolation and purification, e.g. using gel electrophoresis, and subsequent ligation, e.g. using DNA ligase. The fusion protein construct may then be transfected into any suitable host cell, cultured and isolated using standard protein purification techniques.

The construct may also be used as naked DNA or as a plasmid/liposome, plasmid/polyethyleneimine, plasmid/dendrimer or plasmid/peptide complex.

Alternatively, the construct may be introduced into a replication-deficient virus which can be used to target the construct to specific sites in vivo. For example, the construct may be a retroviral vector comprising the appropriate cDNA for the fusion protein. A replication-deficient retrovirus, e.g. Moloney murine retrovirus, may then be used for the stable transfection of target cells and tissues. Other viruses that can be used include replication-deficient adenoviruses, adeno-associated viruses, herpes viruses, papilloma viruses and sinibis viruses. Additional viruses will be apparent to those skilled in the art.

In addition to the functional domains of avidin, streptavidin or related protein, the fusion protein will typically comprise the membrane-spanning domains of endocytotic receptors. The use of these receptors enables the uptake of biotinylated molecules into a target cell. Suitable receptors that may be used in this invention include the scavenger receptor class A, low density lipoprotein receptor, very low density lipoprotein receptor, transferrin receptor and the LOX-1 receptor. The fusion protein may also comprise a linker between the receptor protein and the avidin peptide sequences. The linker may be any length, provided that the functional activity of the different components of the fusion protein is retained.

In general, the fusion between avidin or streptavidin peptide sequences and the receptor peptide sequences is between the extracellular domain of the receptor protein and any site outside of the biotin-binding site of avidin or streptavidin.

The following Example illustrates the invention.

EXAMPLE

A DNA construct was created between the bovine scavenger receptor class A (ScR) (Kodama et al. (1990) Nature 343:531–535) and avidin (Green (1975) Adv. Prot. Chem. 29:85–133), which codes for a protein having a ScR cytoplasmic domain, membrane-spanning domain and α-helical coiled domain, ligated to a biotin-binding domain. The complete amino acid sequence of the fusion protein is shown in SEQ ID No 2 where amino acids 1–53 represent the cytoplasmic domain; amino acids 55–79 represent the transmembrane domain; amino acids 81–111 represent a spacer domain; and amino acids 113–272 represent the α-helical coiled domain. Amino acids 273–400 represent the mature avidin peptide sequence derived from avidin cDNA (Gope et al. (1987) Nucleic Acid Res. 15:3595–3606) lacking a secretion signal.

Briefly, the cDNA for ScR was obtained from cultured cells previously transfected with a plasmid (PLScRNL) containing the ScR cDNA with an internal Rous Sarcoma Virus promoter and HindIII restriction sites. The isolated cDNA was then inserted into a HindIII site of the retrovirus vector pLS1ARNL. The avidin cDNA was produced by the polymerase chain reaction and then inserted into the retrovirus vector at a Sty 1 restriction site on the ScR cDNA. The cDNA embodying the invention is shown as SEQ ID No 1, where nucleotides 1–989 represent a long terminal repeat from Mo-MuSV; nucleotides 1071–2270 represent the coding region for the fusion protein; nucleotides 2376–3101 represent an untranslated region from bovine scavenger receptor I cDNA; nucleotides 3107–3376 represent an RSV promoter region; nucleotides 3727–4522 represent a neo R gene; and nucleotides 4540–5177 represent a long terminal repeat from Mo-MuLV.

Figure 2:
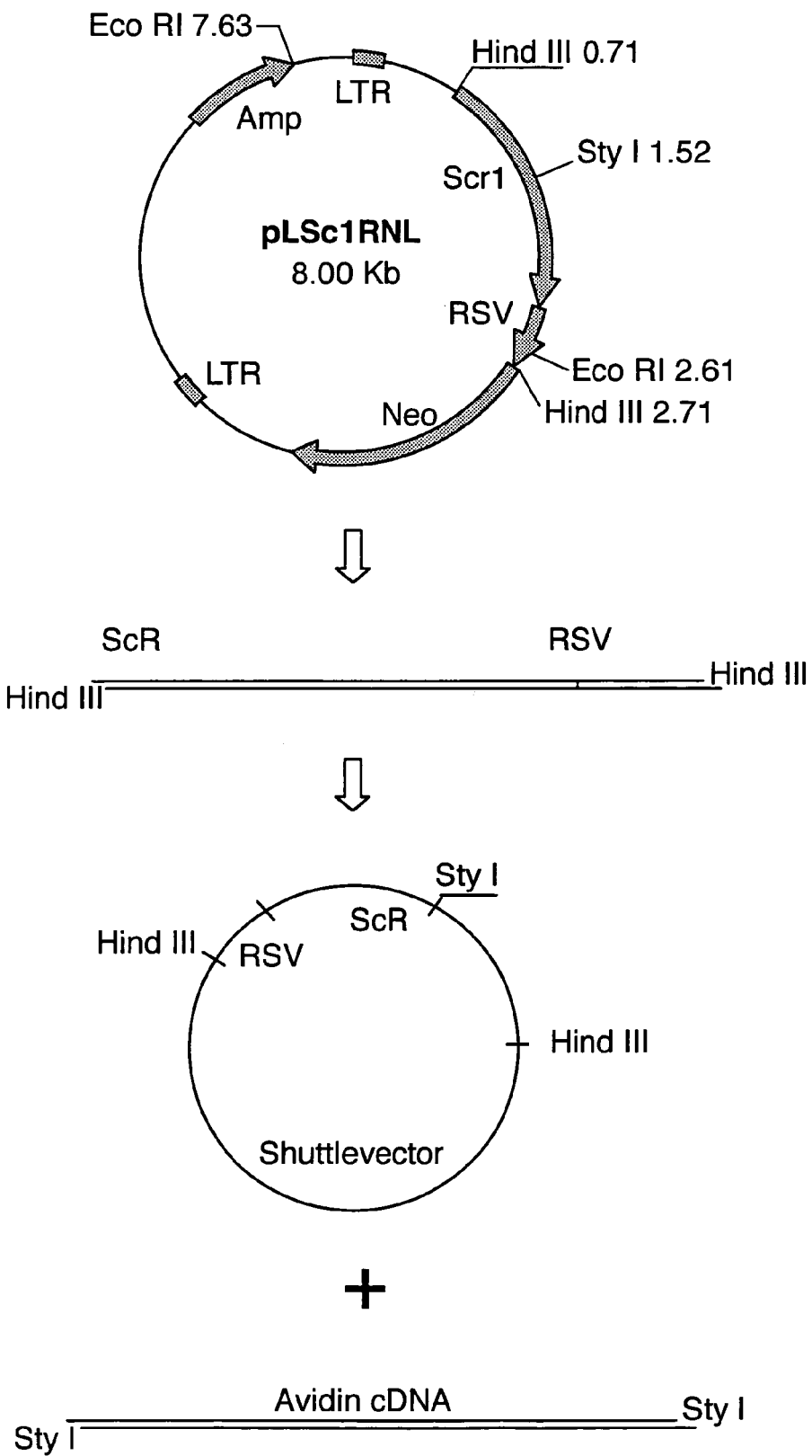
Figure 3:
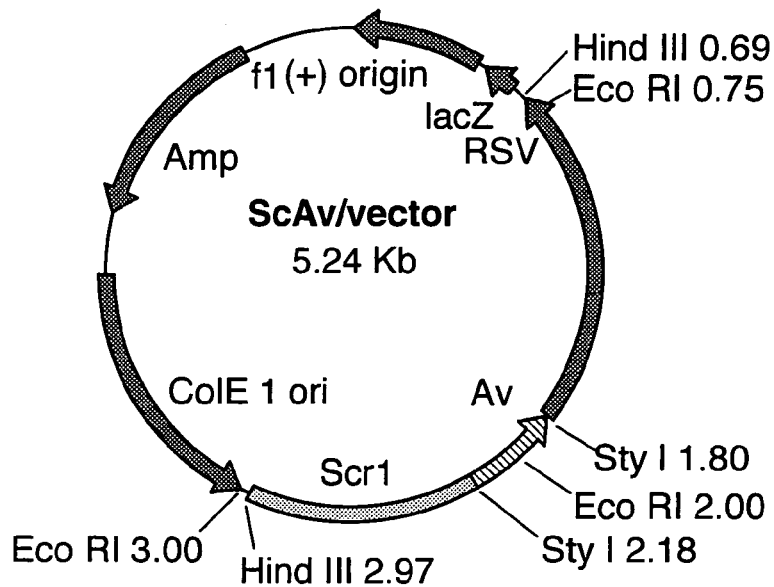
Figure 3:
Figure 3:
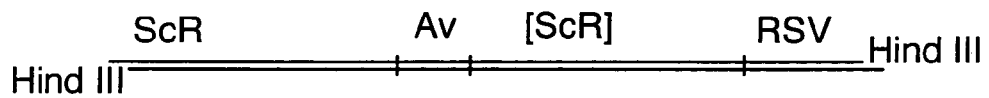
Figure 3:
Figure 3:
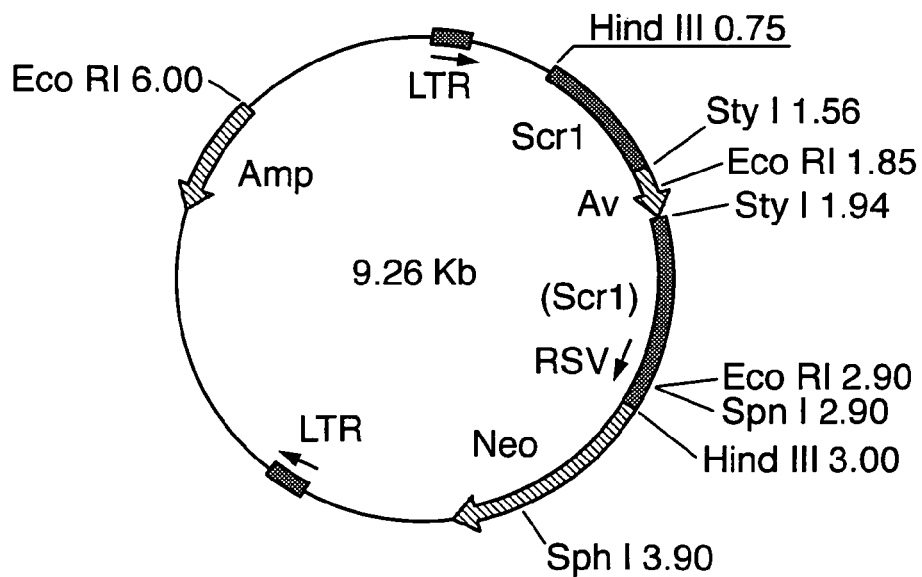

FIGS. 2 and 3 refer to processes used in this Example. More specifically, FIG. 2 shows how the ScR cDNA with an internal RSV promoter was cut from plasmid pLScRNL by HindIII and cloned into a HindIII site of a shuttle vector. FIG. 3 shows how the ScR-avidin-RSV cDNA was cloned into a retrovirus vector pLRNL HindIII site.

The expression of the fusion protein in cells transfected with the vector can be confirmed by Northern blotting and immunocytochemical staining with an antibody raised against avidin.

The experiments revealed that the full mRNA transcript was translated into 55 kDa monomers, which were able to form secondary structures of 110 kDa dimers attached by S—S bonds under non-reducing conditions. Approximately 110 kDa dimeric and 55 kDa monomeric peptides were detected, using denaturing conditions. The result is comparable to the computer calculation for the monomeric fusion protein, 45 kDa. In non-denaturing conditions (i.e. using acetylation prior to Western blotting), the strongest signal was approximately 220 kDa which was denatured to an approximately 110 kDa dimer and a 55 kDa monomer, suggesting the formation of tetramers. The presence of the 220 kDa protein was also verified using chemical cross-linkers, e.g. NHS-esters. The results show that avidin remains soluble and is capable of forming tetramers even when attached to membrane-spanning domains of endocytotic receptors.

The fusion protein was shown to be a functional protein capable of binding FITC-biotin when analysed by confocal microscopy and atomic force microscopy. Untransduced cells and cells transfected with a retrovirus vector containing the LacZ gene were used as controls. No non-specific binding of biotin probes to LacZ-transduced control cells was detected by atomic force microscopy. As expected, the transfected cells showed specific binding that was repeatably measurable in unfixed samples. The measured binding forces were multiples of the average 149±19 pN (mean±sd), which is, as also expected, within the range of the earlier reported biotin-streptavidin binding force of 160 pN (Florin et al (1994), Science 264:415–417).

Functionality of the construct can also be confirmed in vivo by showing the binding of fluorescently-labelled biotin molecules to cells having the fusion protein construct, using FACS analysis.

The functional activity of the fusion protein in vivo was analysed in a rat malignant glioma model. BT4C wild-type glioma cells were implanted intracranially in the right corpus callosum at a depth of 2.5 mm in the brain of inbred BDIX female rats. The growth of tumors was monitored frequently with high resolution MRI (magnetic resonance imaging). Three weeks after tumor cell inoculations, pseudotyped retrovirus carrying cDNA for the fusion protein or LacZ gene in titers of $2\times10^6$ cfu/ml and $1.3\times10^6$ cofu/ml, respectively, was transferred into the tumor, firstly at a depth of 2.5 mm and then at a depth of 1.5 mm, with a 10 minute interval. Gene transfer was repeated after two days of growth. Animals were sacrificed and perfusion-fixed with 4% PFA 3 days after the last injection. Brains were removed and divided at the injection site into two coronal pieces, sectioned on ice and analysed with immunoreactivity against anti-avidin antibody. The results showed that the fusion protein was expressed in vivo in rat malignant glioma. Protein was detected in glioma cells and in ring-like structures resembling vascular endothelial cells in tumor blood vessels.

We claim:

1. An isolated nucleic acid molecule encoding a protein comprising a membrane-spanning domain of an endocytotic receptor and an extracellular domain, wherein said extracellular domain binds biotin, and wherein said protein encoded by said nucleic acid molecule comprises the amino acid sequence shown in SEQ ID NO. 2.

2. A recombinant expression vector comprising a nucleic acid molecule according to claim 1.

3. The recombinant expression vector according to claim 2, wherein said nucleic acid molecule comprises the nucleotide sequence of nucleotides 1071–2270 of SEQ ID NO. 1.

4. The recombinant expression vector according to claim 2, wherein said expression vector is a retrovirus vector.

5. A process for the production of a protein that comprises the amino acid sequence as shown in SEQ ID NO: 2, said process comprising transfecting cells with a recombinant expression vector according to claim 2, and expressing said protein in the transfected cells.

* * * * *

SEQUENCE LISTING

```
<160> NUMBER OF SEQ ID NOS: 2

<210> SEQ ID NO 1
<211> LENGTH: 5177
<212> TYPE: DNA
<213> ORGANISM: Artificial Sequence
<220> FEATURE:
<223> OTHER INFORMATION: Recombinant cDNA encoding fusion protein
<220> FEATURE:
<221> NAME/KEY: CDS
<222> LOCATION: (1071)..(2270)
<223> OTHER INFORMATION:

<400> SEQUENCE: 1
tttgaaagac cccacccgta ggtggcaagc tagcttaagt aacgccactt tgcaaggcat      60
```

-continued

| | |
|---|---|
| ggaaaaatac ataactgaga atagaaaagt tcagatcaag gtcaggaaca aagaaacagc | 120 |
| tgaataccaa acaggatatc tgtggtaagc ggttcctgcc ccggctcagg gccaagaaca | 180 |
| gatgagacag ctgagtgatg ggccaaacag gatatctgtg gtaagcagtt cctgccccgg | 240 |
| ctcggggcca agaacagatg gtccccagat gcggtccagc cctcagcagt ttctagtgaa | 300 |
| tcatcagatg tttccagggt gccccaagga cctgaaaatg accctgtacc ttatttgaac | 360 |
| taaccaatca gttcgcttct cgcttctgtt cgcgcgcttc cgctctccga gctcaataaa | 420 |
| agagcccaca cccctcact cggcgcgcca gtcttccgat agactgcgtc gcccgggtac | 480 |
| ccgtattccc aataaagcct cttgctgttt gcatccgaat cgtggtctcg ctgttccttg | 540 |
| ggagggtctc ctctgagtga ttgactaccc acgacggggg tctttcattt ggggctcgt | 600 |
| ccgggatttg gagacccctg cccagggacc accgacccac caccgggagg taagctggcc | 660 |
| agcaacttat ctgtgtctgt ccgattgtct agtgtctatg tttgatgtta tgcgcctgcg | 720 |
| tctgtactag ttagctaact agctctgtat ctggcggacc cgtggtggaa ctgacgagtt | 780 |
| ctgaacaccc ggccgcaacc ctgggagacg tcccaggac tttgggggcc gttttgtgg | 840 |
| cccgacctga ggaagggagt cgatgtggaa tccgaccccg tcaggatatg tggttctggt | 900 |
| aggagacgag aacctaaaac agttcccgcc tccgtctgaa tttttgcttt cggtttggaa | 960 |
| ccgaagccgc gcgtcttgtc tgctgcagcc aagcttgggc tgcaggtcga ctctagagga | 1020 |
| tcaattcggc acgagtaaat cggtgctgcc gtctttagga catatgaagt atg gca | 1076 |
|                                                                                                             Met Ala<br>                                                                                                              1 | |
| cag tgg gat gac ttt cct gat cag caa gag gac act gac agc tgt aca<br>Gln Trp Asp Asp Phe Pro Asp Gln Gln Glu Asp Thr Asp Ser Cys Thr<br>        5                    10                      15 | 1124 |
| gag tct gtg aag ttc gat gct cgc tca gtg aca gct ttg ctt cct ccc<br>Glu Ser Val Lys Phe Asp Ala Arg Ser Val Thr Ala Leu Leu Pro Pro<br>    20                    25                      30 | 1172 |
| cat cct aaa aat ggc cca act ctt caa gag agg atg aag tct tat aaa<br>His Pro Lys Asn Gly Pro Thr Leu Gln Glu Arg Met Lys Ser Tyr Lys<br>35                      40                      45                      50 | 1220 |
| act gca ctg atc acc ctt tat ctc att gtg ttt gta gtt ctc gtg ccc<br>Thr Ala Leu Ile Thr Leu Tyr Leu Ile Val Phe Val Val Leu Val Pro<br>                55                      60                      65 | 1268 |
| atc att ggc ata gtg gca gct cag ctc ctg aaa tgg gaa acg aag aat<br>Ile Ile Gly Ile Val Ala Ala Gln Leu Leu Lys Trp Glu Thr Lys Asn<br>              70                      75                      80 | 1316 |
| tgc acg gtt ggc tca gtt aat gca gat ata tct cca agt ccg gaa ggc<br>Cys Thr Val Gly Ser Val Asn Ala Asp Ile Ser Pro Ser Pro Glu Gly<br>                85                      90                      95 | 1364 |
| aaa gga aat ggc agt gaa gat gaa atg aga ttt cga gaa gct gtg atg<br>Lys Gly Asn Gly Ser Glu Asp Glu Met Arg Phe Arg Glu Ala Val Met<br>    100                    105                    110 | 1412 |
| gaa cgc atg agc aac atg gaa agc aga atc cag tat ctt tca gat aat<br>Glu Arg Met Ser Asn Met Glu Ser Arg Ile Gln Tyr Leu Ser Asp Asn<br>115                    120                    125                    130 | 1460 |
| gaa gcc aat ctc cta gat gct aag aat ttc caa aat ttc agc ata aca<br>Glu Ala Asn Leu Leu Asp Ala Lys Asn Phe Gln Asn Phe Ser Ile Thr<br>                135                    140                    145 | 1508 |
| act gat caa aga ttt aat gat gtt ctt ttc cag cta aat tcc tta ctt<br>Thr Asp Gln Arg Phe Asn Asp Val Leu Phe Gln Leu Asn Ser Leu Leu<br>              150                    155                    160 | 1556 |
| tcc tcc atc cag gaa cat gag aat atc ata ggg gat atc tcc aag tca<br>Ser Ser Ile Gln Glu His Glu Asn Ile Ile Gly Asp Ile Ser Lys Ser<br>                165                    170                    175 | 1604 |

-continued

| | | |
|---|---|---|
| tta gta ggt ctg aac acc aca gta ctt gat ttg cag ttc agt att gaa<br>Leu Val Gly Leu Asn Thr Thr Val Leu Asp Leu Gln Phe Ser Ile Glu<br>180                              185                            190 | 1652 |
| aca ctg aat ggc aga gtc caa gag aat gca ttt aaa caa caa gag gag<br>Thr Leu Asn Gly Arg Val Gln Glu Asn Ala Phe Lys Gln Gln Glu Glu<br>195                              200                          205                210 | 1700 |
| atg cgt aaa tta gag gag cgt ata tac aat gca tca gca gaa att aag<br>Met Arg Lys Leu Glu Glu Arg Ile Tyr Asn Ala Ser Ala Glu Ile Lys<br>                      215                          220                        225 | 1748 |
| tct cta gat gaa aaa caa gta tat ttg gaa cag gaa ata aaa ggg gaa<br>Ser Leu Asp Glu Lys Gln Val Tyr Leu Glu Gln Glu Ile Lys Gly Glu<br>230                              235                          240 | 1796 |
| atg aaa ctg ttg aat aat atc act aat gat ctg agg ctg aag gat tgg<br>Met Lys Leu Leu Asn Asn Ile Thr Asn Asp Leu Arg Leu Lys Asp Trp<br>                      245                          250                        255 | 1844 |
| gaa cat tct cag aca ttg aaa aat atc act tta ctc caa ggt gcc aga<br>Glu His Ser Gln Thr Leu Lys Asn Ile Thr Leu Leu Gln Gly Ala Arg<br>260                              265                          270 | 1892 |
| aag tgc tcg ctg act ggg aaa tgg acc aac gat ctg ggc tcc aac atg<br>Lys Cys Ser Leu Thr Gly Lys Trp Thr Asn Asp Leu Gly Ser Asn Met<br>275                              280                          285                290 | 1940 |
| acc atc ggg gct gtg aac agc aga ggt gaa ttc aca ggc acc tac atc<br>Thr Ile Gly Ala Val Asn Ser Arg Gly Glu Phe Thr Gly Thr Tyr Ile<br>                      295                          300                        305 | 1988 |
| aca gcc gta aca gcc aca tca aat gag atc aaa gag tca cca ctg cat<br>Thr Ala Val Thr Ala Thr Ser Asn Glu Ile Lys Glu Ser Pro Leu His<br>310                              315                          320 | 2036 |
| ggg aca caa aac acc atc aac aag agg acc cag ccc acc ttt ggc ttc<br>Gly Thr Gln Asn Thr Ile Asn Lys Arg Thr Gln Pro Thr Phe Gly Phe<br>                      325                          330                        335 | 2084 |
| acc gtc aat tgg aag ttt tca gag tcc acc act gtc ttc acg ggc cag<br>Thr Val Asn Trp Lys Phe Ser Glu Ser Thr Thr Val Phe Thr Gly Gln<br>340                              345                          350 | 2132 |
| tgc ttc ata gac agg aat ggg aag gag gtc ctg aag acc atg tgg ctg<br>Cys Phe Ile Asp Arg Asn Gly Lys Glu Val Leu Lys Thr Met Trp Leu<br>355                              360                          365                370 | 2180 |
| ctg cgg tca agt gtt aat gac att ggt gat gac tgg aaa gct acc agg<br>Leu Arg Ser Ser Val Asn Asp Ile Gly Asp Asp Trp Lys Ala Thr Arg<br>                      375                          380                        385 | 2228 |
| gtc ggc atc aac atc ttc act cgc ctg cgc aca cag aag gag<br>Val Gly Ile Asn Ile Phe Thr Arg Leu Arg Thr Gln Lys Glu<br>390                              395                          400 | 2270 |
| tgagtgagtg accaaggtcc tcctggactc caggtgaaaa aggagataga ggccctcctg | 2330 |
| gacaaaatgg tataccaggc tttccaggtc taataggtac tccaggtctt aaaggtgatc | 2390 |
| gggggatct ctggtttacc tggagttcga ggattcccag gaccaatggg gaagaccggg | 2450 |
| aagccaggac ttaatggaca aaaaggccag aagggagaaa aagggagtgg aagcatgcaa | 2510 |
| agacaatcta atacagtccg actggtgggt ggcagcggcc ctcacgaagg cagagtggag | 2570 |
| attttttcacg aaggccagtg gggtacggtg tgtgacgacc gctgggaact gcgtggagga | 2630 |
| ctggtcgtct gcaggagctt gggatacaaa ggtgttcaaa gtgtgcataa gcgagcttat | 2690 |
| tttggaaaag gtacgggtcc aatatggctg aatgaagtat tttgtttcgg gaaagagtca | 2750 |
| tccattgaag agtgcagaat tagacagtgg ggtgtgagag cctgttcgca cgacgaagat | 2810 |
| gctgggggtc actttgcacc tacataatgc atcatatttt cattcacatt ttttaaactg | 2870 |
| ttataaagtg atttttttcc tttgcttcac taaaatcagc ttaattaata tttaagaaac | 2930 |

-continued

```
taagaattttt atccacagaa aaggaatatt taaaaatcac tggataaaca tataaaatag    2990
cttcatattt gcttcaaata ccagaaccat ttcaacttct ctaggttttt aagtggctcg    3050
tgccgaattg atcccctcag gatatagtag tttcgctttt gcatagggag ggggaaatgt    3110
agtcttatgc aatactcttg tagtcttgca acatggtaac gatgagttag caacatgcct    3170
tacaaggaga gaaaaagcac cgtgcatgcc gattggtgga agtaaggtgg tacgatcgtg    3230
ccttattagg aaggcaacag acgggtctga catggattgg acgaaccact gaattccgca    3290
ttgcagagat attgtattta agtgcctagc tcgatacagc aaacgccatt tgaccattca    3350
ccacattggt gtgcacctcc aagcttcacg ctgccgcaag cactcagggc gcaagggctg    3410
ctaaaggaag cggaacacgt agaaagccag tccgcagaaa cggtgctgac cccggatgaa    3470
tgtcagctac tgggctatct ggacaaggga aaacgcaagc gcaaagagaa agcaggtagc    3530
ttgcagtggg cttacatggc gatagctaga ctgggcggtt ttatggacag caagcgaacc    3590
ggaattgcca gctggggcgc cctctggtaa ggttgggaag ccctgcaaag taaactggat    3650
ggctttcttg ccgccaagga tctgatggcg caggggatca agatctgatc aagagacagg    3710
atgaggatcg tttcgcatga ttgaacaaga tggattgcac gcaggttctc cggccgcttg    3770
ggtggagagg ctattcggct atgactgggc acaacagaca atcggctgct ctgatgccgc    3830
cgtgttccgg ctgtcagcgc aggggcgccc ggttcttttt gtcaagaccg acctgtccgg    3890
tgccctgaat gaactgcagg acgaggcagc gcggctatcg tggctggcca cgacgggcgt    3950
tccttgcgca gctgtgctcg acgttgtcac tgaagcggga agggactggc tgctattggg    4010
cgaagtgccg gggcaggatc tcctgtcatc tcaccttgct cctgccgaga agtatccat    4070
catggctgat gcaatgcggc ggctgcatac gcttgatccg gctacctgcc cattcgacca    4130
ccaagcgaaa catcgcatcg agcgagcacg tactcggatg gaagccggtc ttgtcgatca    4190
ggatgatctg gacgaagagc atcaggggct cgcgccagcc gaactgttcg ccaggctcaa    4250
ggcgcgcatg cccgacggcg aggatctcgt cgtgacccat ggcgatgcct gcttgccgaa    4310
tatcatggtg gaaaatggcc gcttttctgg attcatcgac tgtggccggc tgggtgtggc    4370
ggaccgctat caggacatag cgttggctac ccgtgatatt gctgaagagc ttggcggcga    4430
atgggctgac cgcttcctcg tgctttacgg tatcgccgct cccgattcgc agcgcatcgc    4490
cttctatcgc cttcttgacg agttcttctg agcgggactc tggggttcga taaaataaaa    4550
gattttattt agtctccaga aaaggggggg aatgaaagac cccacctgta ggtttggcaa    4610
gctagcttaa gtaacgccat tttgcaaggc atggaaaaat acataactga gaatagaaa    4670
gttcagatca aggtcaggaa cagatggaac agctgaatat gggccaaaca ggatatctgt    4730
ggtaagcagt tcctgccccg gctcaggcc aagaacagat ggaacagctg aatatgggcc    4790
aaacaggata tctgtggtaa gcagttcctg ccccggctca gggccaagaa cagatggtcc    4850
ccagatgcgg tccagccctc agcagtttct agagaaccat cagatgtttc cagggtgccc    4910
caaggacctg aaatgaccct gtgccttatt tgaactaacc aatcagttcg cttctcgctt    4970
ctgttcgcgc gcttctgctc cccgagctca ataaaagagc ccacaacccc tcactcgggg    5030
cgccagtcct ccgattgact gagtcgcccg ggtacccgtg tatccaataa accctcttgc    5090
agttgcatcc gacttgtggt ctcgctgttc cttgggaggg tctcctctga gtgattgact    5150
acccgtcagc gggggtcttt catttgg                                        5177
```

<210> SEQ ID NO 2
<211> LENGTH: 400

```
<212> TYPE: PRT
<213> ORGANISM: Artificial Sequence
<220> FEATURE:
<223> OTHER INFORMATION: Recombinant cDNA encoding fusion protein

<400> SEQUENCE: 2

Met Ala Gln Trp Asp Phe Pro Asp Gln Glu Asp Thr Asp Ser
1               5                   10                  15

Cys Thr Glu Ser Val Lys Phe Asp Ala Arg Ser Val Thr Ala Leu Leu
            20                  25                  30

Pro Pro His Pro Lys Asn Gly Pro Thr Leu Gln Glu Arg Met Lys Ser
        35                  40                  45

Tyr Lys Thr Ala Leu Ile Thr Leu Tyr Leu Ile Val Phe Val Val Leu
    50                  55                  60

Val Pro Ile Ile Gly Ile Val Ala Ala Gln Leu Leu Lys Trp Glu Thr
65                  70                  75                  80

Lys Asn Cys Thr Val Gly Ser Val Asn Ala Asp Ile Ser Pro Ser Pro
                85                  90                  95

Glu Gly Lys Gly Asn Gly Ser Glu Asp Glu Met Arg Phe Arg Glu Ala
            100                 105                 110

Val Met Glu Arg Met Ser Asn Met Glu Ser Arg Ile Gln Tyr Leu Ser
        115                 120                 125

Asp Asn Glu Ala Asn Leu Leu Asp Ala Lys Asn Phe Gln Asn Phe Ser
    130                 135                 140

Ile Thr Thr Asp Gln Arg Phe Asn Asp Val Leu Phe Gln Leu Asn Ser
145                 150                 155                 160

Leu Leu Ser Ser Ile Gln Glu His Glu Asn Ile Ile Gly Asp Ile Ser
                165                 170                 175

Lys Ser Leu Val Gly Leu Asn Thr Thr Val Leu Asp Leu Gln Phe Ser
            180                 185                 190

Ile Glu Thr Leu Asn Gly Arg Val Gln Glu Asn Ala Phe Lys Gln Gln
        195                 200                 205

Glu Glu Met Arg Lys Leu Glu Glu Arg Ile Tyr Asn Ala Ser Ala Glu
    210                 215                 220

Ile Lys Ser Leu Asp Glu Lys Gln Val Tyr Leu Glu Gln Glu Ile Lys
225                 230                 235                 240

Gly Glu Met Lys Leu Leu Asn Asn Ile Thr Asn Asp Leu Arg Leu Lys
                245                 250                 255

Asp Trp Glu His Ser Gln Thr Leu Lys Asn Ile Thr Leu Leu Gln Gly
            260                 265                 270

Ala Arg Lys Cys Ser Leu Thr Gly Lys Trp Thr Asn Asp Leu Gly Ser
        275                 280                 285

Asn Met Thr Ile Gly Ala Val Asn Ser Arg Gly Glu Phe Thr Gly Thr
    290                 295                 300

Tyr Ile Thr Ala Val Thr Ala Thr Ser Asn Glu Ile Lys Glu Ser Pro
305                 310                 315                 320

Leu His Gly Thr Gln Asn Thr Ile Asn Lys Arg Thr Gln Pro Thr Phe
                325                 330                 335

Gly Phe Thr Val Asn Trp Lys Phe Ser Glu Ser Thr Thr Val Phe Thr
            340                 345                 350

Gly Gln Cys Phe Ile Asp Arg Asn Gly Lys Glu Val Leu Lys Thr Met
        355                 360                 365
```

-continued

```
Trp Leu Leu Arg Ser Ser Val Asn Asp Ile Gly Asp Asp Trp Lys Ala
    370             375             380

Thr Arg Val Gly Ile Asn Ile Phe Thr Arg Leu Arg Thr Gln Lys Glu
385             390             395             400
```